(12) United States Patent
DeGraaf et al.

(10) Patent No.: US 12,083,029 B2
(45) Date of Patent: *Sep. 10, 2024

(54) CONTROLLED EXTENSION STENT

(71) Applicant: Boston Scientific Scimed, Inc., Maple Grove, MN (US)

(72) Inventors: Kimberly DeGraaf, Holden, MA (US); Timothy P. Harrah, Cambridge, MA (US); Mark W. Boden, Harrisville, RI (US); Jan Seppala, Loretto, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 161 days.

This patent is subject to a terminal disclaimer.

(21) Appl. No.: 17/536,834

(22) Filed: Nov. 29, 2021

(65) Prior Publication Data

US 2022/0079785 A1   Mar. 17, 2022

Related U.S. Application Data

(63) Continuation of application No. 15/802,863, filed on Nov. 3, 2017, now Pat. No. 11,213,414.

(60) Provisional application No. 62/417,484, filed on Nov. 4, 2016.

(51) Int. Cl.
| | | |
|---|---|---|
| *A61F 2/88* | (2006.01) | |
| *A61F 2/04* | (2013.01) | |
| *A61F 2/91* | (2013.01) | |
| *A61M 27/00* | (2006.01) | |
| *A61B 17/00* | (2006.01) | |
| *A61F 2/95* | (2013.01) | |

(52) U.S. Cl.
CPC ............... *A61F 2/91* (2013.01); *A61F 2/042* (2013.01); *A61F 2/88* (2013.01); *A61F 2/885* (2013.01); *A61B 2017/003* (2013.01); *A61F 2002/9511* (2013.01); *A61M 27/008* (2013.01)

(58) Field of Classification Search
CPC .... A61F 2/91; A61F 2/042; A61F 2/88; A61F 2/885; A61F 2002/9511; A61F 2/04; A61F 2/82; A61B 2017/003; A61M 27/008

See application file for complete search history.

(56) References Cited

U.S. PATENT DOCUMENTS

| | | | |
|---|---|---|---|
| 4,813,925 A | | 3/1989 | Anderson, Jr. et al. |
| 5,514,176 A | * | 5/1996 | Bosley, Jr. ............... A61F 2/88 |
| | | | 606/191 |
| 5,681,274 A | | 10/1997 | Perkins et al. |

(Continued)

FOREIGN PATENT DOCUMENTS

| | | |
|---|---|---|
| CN | 2180285 Y | 10/1994 |
| CN | 201194856 Y | 2/2009 |

(Continued)

OTHER PUBLICATIONS

International Search Report and Written Opinion dated (Feb. 21, 2018), for PCT/US17/59868 (12 pages).

*Primary Examiner* — Kai H Weng
*Assistant Examiner* — Alessandro R Del Priore
(74) *Attorney, Agent, or Firm* — Seager, Tufte & Wickhem, LLP

(57) ABSTRACT

The present disclosure relates generally to controlled extension medical stents, and more particularly to controlled extension devices positioned in the body to stent the ureter and facilitate drainage from the kidney to the bladder.

17 Claims, 9 Drawing Sheets

(56) References Cited

U.S. PATENT DOCUMENTS

| | | | |
|---|---|---|---|
| 5,749,919 A * | 5/1998 | Blanc | A61F 2/88 606/198 |
| 6,090,115 A * | 7/2000 | Beyar | A61F 2/88 606/113 |
| 6,425,915 B1 | 7/2002 | Khosravi et al. | |
| 7,044,981 B2 | 5/2006 | Liu et al. | |
| 7,169,187 B2 | 1/2007 | Datta et al. | |
| 7,507,218 B2 | 3/2009 | Aliski et al. | |
| 7,789,915 B2 | 9/2010 | Lavelle et al. | |
| 7,951,206 B2 | 5/2011 | St. Pierre | |
| 8,597,367 B2 | 12/2013 | Dillinger | |
| 8,728,169 B2 | 5/2014 | Li | |
| 2004/0087886 A1* | 5/2004 | Gellman | A61M 27/008 604/8 |
| 2005/0033410 A1 | 2/2005 | Hogendijk et al. | |
| 2005/0043783 A1* | 2/2005 | Amis | A61F 2/88 623/1.22 |
| 2005/0240277 A1* | 10/2005 | Aliski | A61F 2/04 604/8 |
| 2007/0276466 A1 | 11/2007 | Lavelle et al. | |
| 2008/0177368 A1* | 7/2008 | Goto | A61F 2/95 623/1.11 |
| 2011/0152906 A1* | 6/2011 | Escudero | A61B 17/3207 606/159 |
| 2014/0257463 A1 | 9/2014 | Sweeney et al. | |
| 2016/0249882 A1* | 9/2016 | Degertekin | A61B 1/05 600/424 |

FOREIGN PATENT DOCUMENTS

| | | |
|---|---|---|
| JP | 2002253681 A | 9/2002 |
| JP | 2005013733 A | 1/2005 |
| JP | 2006198733 A | 8/2006 |
| JP | 2012214007 A | 11/2012 |
| WO | 9313824 A1 | 7/1993 |

* cited by examiner

CONTROLLED EXTENSION STENT

PRIORITY

This application is a continuation of Ser. No. 15/802,863, filed Nov. 3, 2017, which claims the benefit of priority under 35 U.S.C. § 119 to U.S. Provisional Patent Application Ser. No. 62/417,484, filed Nov. 4, 2016, which is incorporated by reference in its entirety and for all purposes.

FIELD

The present disclosure relates generally to controlled extension stents, and more particularly to controlled extension stents positioned in the body to stent the ureter and facilitate drainage from the kidney to the bladder. A stent of the disclosure may include a plurality of filaments wound in adjacent groups of coils, each group including the plurality of filaments, the adjacent groups defining a lumen about a longitudinal axis of the stent along the length of the stent, the adjacent groups in substantial contact with neighboring adjacent groups in a non-extended state and separated from neighboring adjacent groups in an extended state. The stent may include a dissolvable coating. Methods of manufacturing controlled extension stents and procedures for the use of controlled extension stents in the treatment of patients are also disclosed.

BACKGROUND

Stents developed for implantation or insertion into patients are known for various purposes including stenting, drainage, etc., of lumens, tracts, vessels, and cavities within the body. As an example, polymeric ureteral stents are widely used to facilitate drainage in the upper urinary tract (e.g., drainage from the kidney to the bladder), for example, following ureteroscopy, endourerotomies, and endopyelotomy for ureteral strictures, as well as in other instances where ureteral obstruction may occur.

An exemplary stent 10 of this type is illustrated in FIG. 1. The stent 10 has a proximal end 10p and a distal end 10d. It is a tubular polymer extrusion having a shaft 12, a distal renal retention member (e.g., renal "pigtail" 14), and a proximal retention member (e.g., bladder "pigtail" 16). These retention members when present prevent upward migration of the stent toward the kidney or downward migration of the stent toward the bladder. Once properly deployed in the ureter, the stent 10 supports the ureter and allows the passage of urine through the stent and, since the ureter naturally dilates around foreign bodies, allows urine to flow around the stent as well. The stent 10, as exemplified by FIG. 1, may further be provided with any one or more of the following: (a) a tapered tip 11, to aid insertion, (b) multiple side ports 18 (one numbered), which may be arranged in a spiral pattern down the length of the body to promote drainage, (c) graduation marks 25 (one illustrated), which are normally used for visualization by the physician to know when the appropriate length of stent has been inserted into the ureter, and (d) a suture 22, which aids in positioning and withdrawal of the stent.

During placement, such ureteral stents 10 may be typically placed over a urology guide wire, through a cystoscope or flexible ureteroscope, and advanced into position with a pusher and/or other positioning device that may engage and release the stent 10. Once the distal end of the stent is advanced into the kidney/renal calyx, the guide wire is removed, allowing retention members, such as pigtails 14, 16, to form in the kidney 19 and bladder 20, as shown in FIG. 2. The renal pigtail 14 of the stent may be closed or tapered on the end, depending on the method of insertion (e.g., the use of a guide wire or otherwise). As shown in FIG. 2, the stent 10 extends through the ureteral orifice 21a and into the bladder 20. For clarity, the ureter entering bladder 20 through the opposite ureteral orifice 21b is not shown.

These types of implanted stents may be associated with patient discomfort or pain after being positioned within the body, for example, in regard to ureteral stents, pain and/or discomfort in the bladder and flank area after insertion. Another potential issue is that various applications and anatomies require stents of different diameters and lengths, e.g., differences in individual ureteral anatomies require different diameters and lengths between the end retention members of ureteral stents. Consequently, hospitals and other facilities inventory stents of different diameters and for each diameter, stents of different lengths, in some cases as much as six stents of different lengths for each diameter.

Generally, a physician must estimate ureter length before beginning a procedure. If the estimate is near the end of a particular length range, it is possible to select a stent that is slightly too long or too short. However, that fact may not be ascertainable until the stent has been implanted. The procedure for correcting any incorrect selection may involve removing that stent and placing a longer or shorter stent in the ureter thereby complicating the procedure and potentially increasing patient trauma.

Variable length stents may include offset or planar coils as one or both of the end retention members that can be unwound to increase or decrease the effective length between the structures. Another ureteral stent example includes a stent with multiple coils at the bladder end that may be clipped off outside of the body when the length of the stent has been estimated by the physician.

Although these examples may reduce inventory requirements, excess retention member left in the bladder may occupy a considerable volume which may increase a risk of tissue irritation. Additionally, stents clipped to length outside of the body prior to placement without reference markings may ultimately result in a length that is too short, requiring a new stent to be used, or too long, in which case the excess material and irritation concerns remain. Even if the estimated length is correct at the time of positioning the stent, a patient's body movements may cause the stent to migrate out of position. Therefore, there exists a need for stents and methods of use for stents that are capable of controlled extension.

SUMMARY

The present disclosure, in its various aspects, meets an ongoing need in the medical field, generally with respect to stents and more particularly with respect to ureteral stents, for stents capable of controlled extension to fit the various lengths of anatomies and extensions to allow for patient body movement.

A stent may comprise a plurality of filaments wound in adjacent groups of coils. The coils of the groups may include each of the plurality of filaments, with the adjacent groups defining a lumen about a longitudinal axis of the stent along the length of the stent. The adjacent groups may be in substantial contact with neighboring adjacent groups in a non-extended state and separated from neighboring adjacent groups in an extended state.

A stent may have its groups of coils tacked together on at least one substantially helical contact line running between the groups along at least portions of the stent length. A stent may further comprise a reflowed substantially smooth outer surface along the at least one substantially helical contact line. A stent may have filaments separate from each other within the groups of coils.

A stent may include a proximal and a distal end of the stent each having an annular tail. A stent may include certain groups at a distal end of the stent forming a spiraled cone-shape, the cone-shape widening in diameter toward the distal end of the stent. Certain of the adjacent groups in the non-extended state may be tacked together and certain of the adjacent groups may not be tacked together. At least one end of a stent may be a straight filament. A stent may include a difference in length between the extended state and the non-extended state to be a range of about three centimeters to about ten centimeters. A stent may include filaments that have a cross-section that is circular, oblong, star-shaped, or the like. A stent may include certain of the coils of filaments in adjacent groups overlapping each other in a telescoping fashion. A stent may include certain coils lying in a plane substantially perpendicular to the longitudinal axis. A stent may include certain coils lying in a plane at an angle from the longitudinal axis that ranges from 10 degrees to 90 degrees.

A stent may comprise a filament wound in coils about a longitudinal axis of the stent and along the length of the stent in a substantially helical pattern. The coils may define a lumen along the longitudinal axis through the center of the pattern. Adjacent coils of the filament may be in substantial contact in a non-extended state and not in substantial contact in an extended state. A stent may include a filament with a substantially flattened rectangular cross-section with rounded corners. A stent may include a filament with a ribbon wound in the adjacent coils.

A method of creating a stent may include winding a plurality of filaments in adjacent groups around a mandrel. The groups may include coils of each of the plurality of filaments. The coils of the plurality of filaments may be wound in an alternating fashion. The coils of the plurality of filaments in adjacent groups may define a stent body with a distal end portion, a proximal end portion, a lumen running therethrough and a length. A method may include tacking one or more adjacent groups together at select locations along the length of the stent. The tacking may be permanent or temporary. A method may include applying a dissolvable coating to portions of the stent body. A method may include straightening the coils at either or both of the distal and proximal end portions of the stent, fusing the filaments together along the portions and forming the fused portions into retention members. A method may include setting retention members separately from a stent body and then attaching them to the stent body, for example, by bonding the members to the body. A dissolvable coating may be applied to a stent body prior to or after attaching retention members, so that a coated stent body with attached uncoated or coated retention members may be possible.

A method of treating a patient may comprise introducing a stent into the patient. The stent may comprise groups of coils of one or more filaments forming a lumen of the stent along its length. The groups of coils may be configured to allow controlled extension of the stent along the length cooperatively with the patient's movement. Controlled extension may take place between certain of the groups of coils, or between certain of the coils within the groups of coils, or both. A method of treating a patient may include introducing into a ureter of the patient a stent with a distal retention member that is placed into the kidney of the patient. A method may include introducing into a ureter of the patient a stent with a proximal retention member that is placed into the bladder of the patient.

A stent may include a dissolvable coating along the length of the stent in at least a non-extended state. The coating may be disposed about portions of a filament or a plurality of filaments, which may be in coils about the longitudinal axis of the stent and define a lumen of the stent. The coating may comprise polyvinyl alcohol. The coating may be configured to dissolve within a certain range of time after a stent is implanted in the body of a patient. The relative flexibility/rigidity or controlled extension, or both, of a stent may be affected by the coating when it is present and as it dissolves. Lubricity and surface friction of a stent may be affected by the coating, as well.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures.

Figure 1:
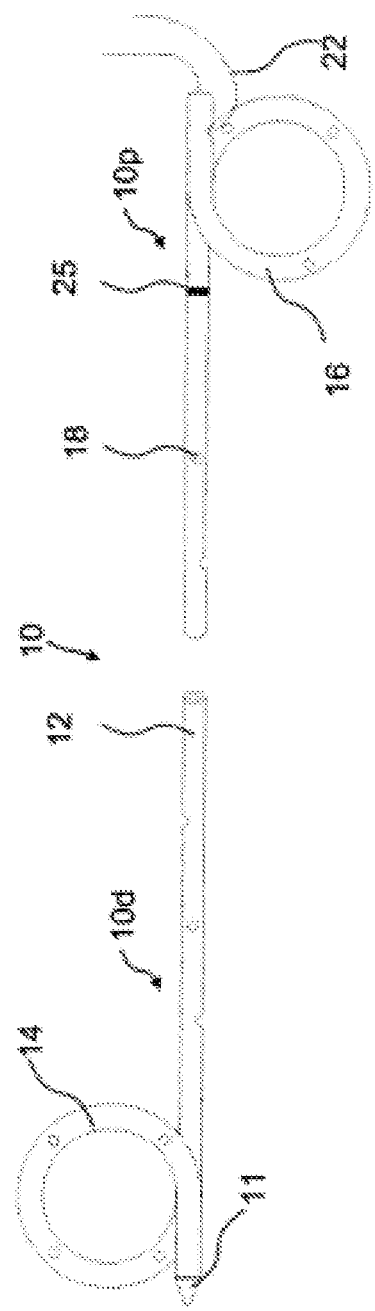
FIG. 1 is an illustration of a ureteral stent, according to the prior art.
Figure 2:
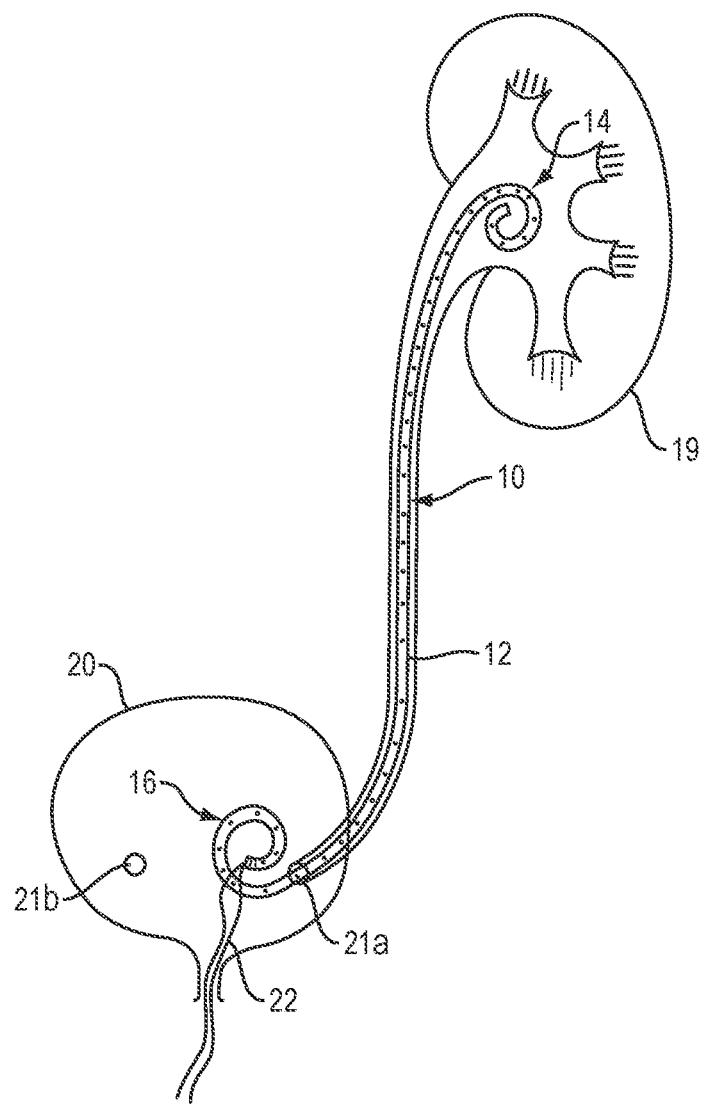
FIG. 2 is an illustration of a prior art ureteral stent, like that of FIG. 1, positioned in the body.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Devices, systems and methods in accordance with various embodiments of the present disclosure include controlled extension stents, particularly ureteral stents. In one or more embodiments, such stents may include a single filament coiled about an axis along the length of the stent or multiple filaments wound in adjacent groups of coils that define a lumen about a longitudinal axis of the stent. Adjacent coils of a single filament or adjacent groups of coils with multiple filaments may be in substantial contact with other adjacent coils or with neighboring adjacent groups in a non-extended state and may be separated in an extended state.

Various embodiments of the stents of the present disclosure provide comfort to a recipient patient. A controlled extension stent may provide a response to a patient's body movement that may reduce irritation in areas including the kidney, ureter, and bladder. A controlled extension stent may also aid in keeping the stent in position within the patient rather than migrating to an undesirable position. The disclosure includes devices, kits, systems, methods of use, and methods of manufacture of controlled extension stents.

In one or more embodiments, a controlled extension stent may have groups of wound coils or coils of a single filament tacked together on a contact line created by the coils as they wind along the length of the stent. The winding may be in a helical manner. Tacking may be achieved through heat setting above the softening point of filament materials while the coils are in contact with each other or by a permanent or dissolvable adhesive applied along the contact line or lines. Temperature ranges to achieve tacking are dependent on the materials used. The strength of the tack varies with heating temperature and time. This may be accomplished, for example, in a dry oven, a water bath, or by using an RF generator at low voltage. For example, with ethylene-vinyl acetate (EVA), parameters for heat setting may include a heat temperature of 70-80° C. with a set time of 30 minutes to 4 hours. Adhesive tacking may be accomplished using a coating composition such as polyvinylpyrrolidone (PVP). Dissolution time may vary based on adhesion to the substrate, composition, and curing (crosslinking). Adhesive tacking may also be accomplished via a hard candy shell coating made out of sugar. Tacking may be formed on a contact line along the entire length of a stent or just at certain portions, depending on the desired stent architecture. A stent may include along the length some groups of coils where the filaments are tacked together while other groups of coils are not tacked together.

In one or more embodiments, a controlled extension stent may have groups of coils that separate from a neighboring adjacent groups in an extended state. In addition to this group separation, the coiled filaments within the groups may separate from each other in an extended state of the stent. Whether the coiled filaments separate from each other within their group or among groups may depend on whether the filaments or groups are tacked together, and if so, how strong the tacking bond is between the filaments. A stronger tacking bond between the filaments may result in a stent with a higher resistance to tensile stress or bending, while a weaker or non-existing tacking bond may result in a more compliant stent when succumbing to tensile stress or bending.

The manner in which the stent extends is controllable by various factors in its design. The material selected for each filament may determine its amount of extension. A stiffer material may require more tensile stress to extend, while a more pliable material may extend more easily. Filament materials, dimensions, and processing are discussed below in the present disclosure and play a role in the amount of stent extension as well as stent flexibility. For example, extension control may be determined by the thickness of each filament. A thicker filament may be more resistant to tensile stress than a thinner one. Filament thickness may range from, for example, about 0.020 inches (0.508 millimeters) to about 0.037 inches (0.940 millimeters). Further control of stent extension may be achieved by setting the pitch of the coils relative to the longitudinal axis of the stent. A more acute pitch relative to a longitudinal axis of the stent may more readily extend compared to a more perpendicular pitch. Various ranges of pitch angles of the present disclosure are discussed below. Extension control may also be determined by the processing and type of materials in order to vary the range of stretching that may result under tensile stresses of the stent. The tension with which the coils are wound may also vary the amount of stretching. Examples of filaments may include a variable cross-section along the length, which may be composed of a coextruded inner and outer core of different materials for additional control over extension. Alternatively, the filament may be solid of hollow, and the radial or hoop strength of the coils may be adjusted to control extension. Further control of stent extension may be achieved by the number of filaments grouped together along the stent. A greater number of filaments grouped together may provide more resistance to tensile stresses and thus less extension. Additionally, a stent designed with more surface contact among the coiled filaments may provide more friction in resistance to tensile stresses which may result in less stent extension.

The various embodiments of controlled extension stents according to the present disclosure, including as described above and below, may include any of the following features. The single or plural filaments of the stent may be solid or hollow. Devices, particularly in the context of a ureteral stent, may have an outer diameter of about 3 French to about 9 French, including any half or whole size within that range, and may have an inner lumen diameter of about 0.038 inches (0.0965 cm) to accommodate the profile of standard medical guide wires within the lumen of the stent. Embodiments of the present disclosure for use as ureteral stents may have a non-extended length of about 20 cm (7.87 in) to about 35 cm (13.78 in.) as measured between the retention members. Additional extendable length varies based on all of the parameters previously discussed. Patient respiration may extend a ureter about 3 cm to about 5 cm. A maximum extension may be about 10 cm. Excessive extension may be undesirable upon removal of the stent from the patient. A patient may experience additional discomfort during stent removal if the stent extends so much as to resemble the removal of a string rather than a controlled length of coiled stent.

Various exemplary embodiments according to the present disclosure are described below. As used herein, "proximal end" refers to the end of a device that lies closest to the medical professional or outside the urethral exit (downstream) in the case of a ureteral stent, and "distal end" refers to the end of an implanted or positioned device or object that lies furthest from the medical professional or urethral exit (upstream) when used in the context of a ureteral stent.

Figure 3A:
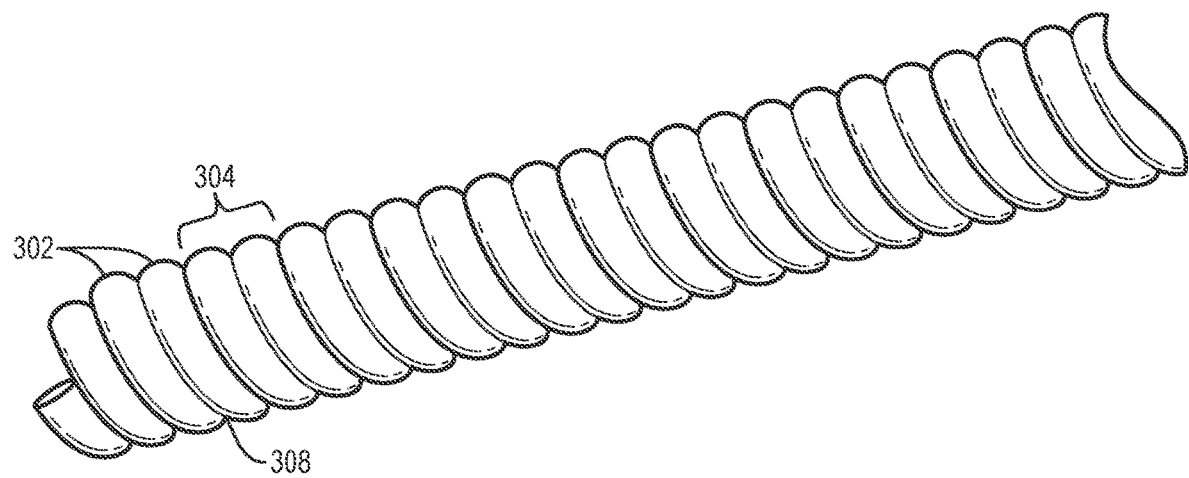
FIG. 3A illustrates a stent in accordance with an embodiment of the present disclosure including two filaments.
Figure 3B:
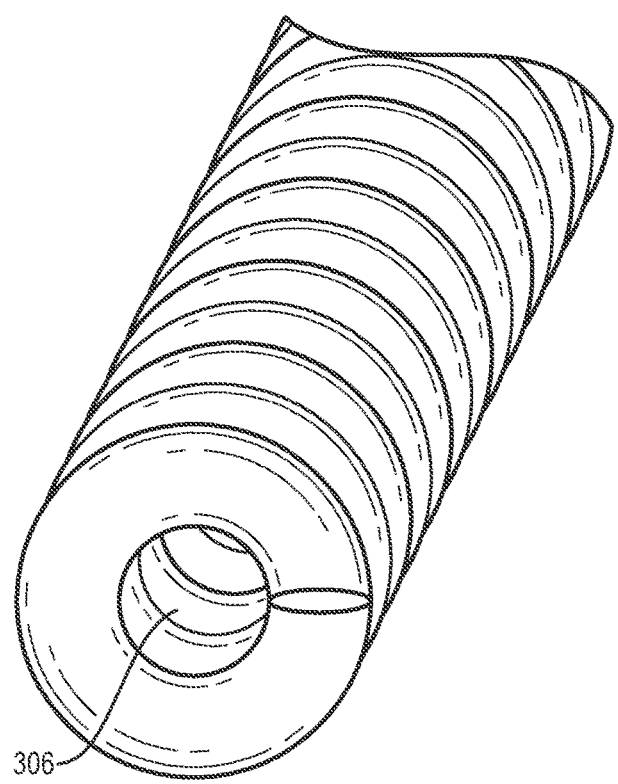
FIG. 3B illustrates a stent in accordance with an embodiment of the present disclosure including two filaments in a non-extended state.

Referring to FIGS. 3A and 3B, an example embodiment of a stent of the present disclosure may include two filaments 302 with a circular cross-section wound in a group of coils 304 adjacent and parallel to each other. The wound group 304 may have a circular or semicircular cross-section to prevent overriding coils during stresses to the stent. The wound groups create a lumen 306 about a longitudinal axis along the length of the stent. In a non-extended state, the two filaments 302 of the stent are in substantial contact with each other along a contact line 308, e.g., a substantially helical contact line that winds about the axis along the length of the stent between the two filaments (as shown) and between groups of coils at the two filaments. The pitch angle depends on various factors, for example, the filament diameter and filament count. For example, the pitch angle may be about 10° to about 60° (including whole and half degrees in between) for the stent ranges disclosed here, measured from the longitudinal axis. The filament count may eventually max out the pitch angle at close to 0° to the stent axis where minimal to non-existent extension will occur. The coils may create a contact line by laying in a plane at an angle from the longitudinal axis in a range of 10° to 90°. The pitch angles may be uniform or alternate along the length of the stent. The contact line may be created by coils that lie in a plane substantially perpendicular to the longitudinal axis of the stent. The contact line may not necessarily be a physical bonding of the two filaments to form the group 304. Alternatively, the contact line 308 may at least partially be a bond between the two filaments 302 that create the group 304 via tacking through heat setting above the softening point of the material while the coils are in contact with each other or the bond may be created with an adhesive.

The coils may be created by winding the filaments around a mandrel to form a lumen for a guide wire, bodily fluid passage, and/or a tubular structure to support ureter function. These coils may provide column strength to prevent buckling and overriding within the patient. This strength may be further increased by tacking the coils and/or filaments together. However, tacking of the coils may be broken with minimal force to provide controlled extension where needed during ureteral movement. The stent may include coils from end to end or may contain sections of coiled and non-coiled filaments. For example, the ends of the stent may include straight filaments or retention members as discussed in the disclosure below.

Figure 4A:
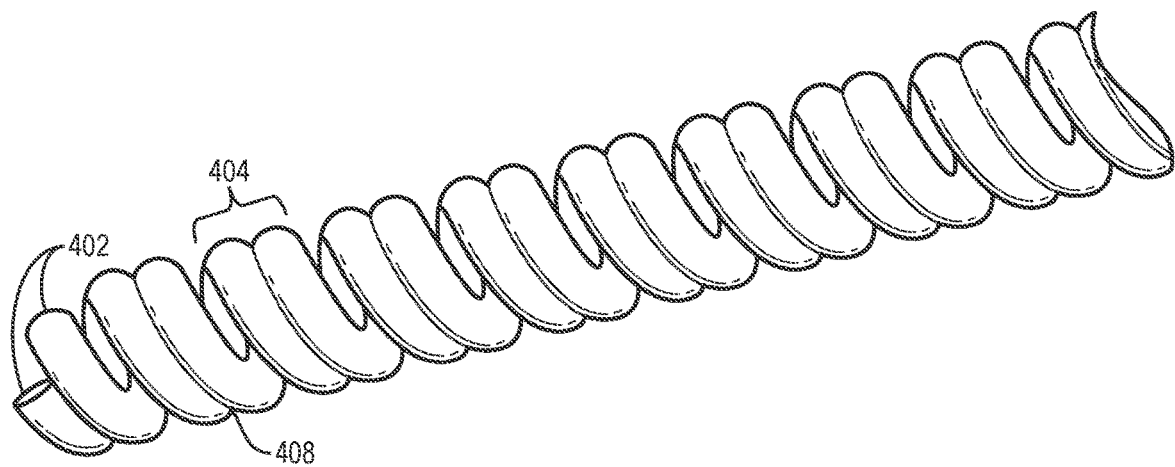
FIG. 4A illustrates a stent in accordance with an embodiment of the present disclosure including two filaments under tensile stress.
Figure 4B:
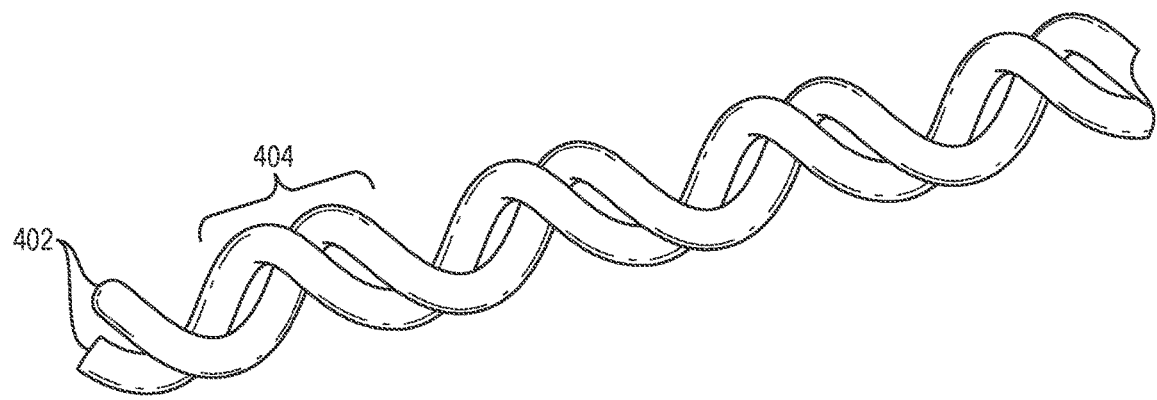
FIG. 4B illustrates a stent in accordance with an embodiment of the present disclosure including two filaments under tensile stress.

Referring to FIG. 4A, a grouping 404 of two filaments 402 of a stent provides a lesser amount of extension under a lesser tensile stress while maintaining its general columnar shape. The contact line 408 may or may not be maintained during this extended state depending on the tacking method chosen (if any at all) for a desired columnar strength. Referring to FIG. 4B, the grouping 404 of the two filaments 402 allows for a greater relative degree of extension under a greater amount of tensile stress while maintaining the grouping's general columnar shape. In this and other stent examples, a range of forces that may result in a range of stent extension of about 0.5 pound-force to a maximum of about 1 pound-force. Typical desired extension range among adult patients is from around 3 cm-10 cm based on nominal ranges of stent length in an non-extended state from 20 cm to 35 cm. The contact line 408 may or may not be maintained. The contact line 408 may provide some tension between filaments in a group 404, even more so if it is tacked. The frequency and location of tacking may be varied along the length of the stent as desired. Surface contact between the groupings of filaments may also provide some tension between the groups because of friction.

Figure 5A:
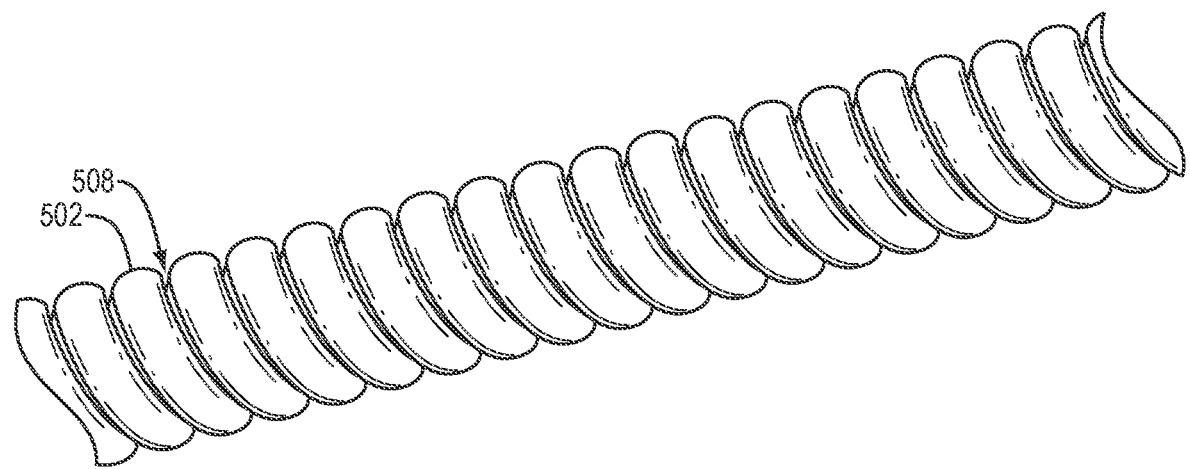
FIG. 5A illustrates a stent in accordance with an embodiment of the present disclosure including one filament in a non-extended state.
Figure 5B:
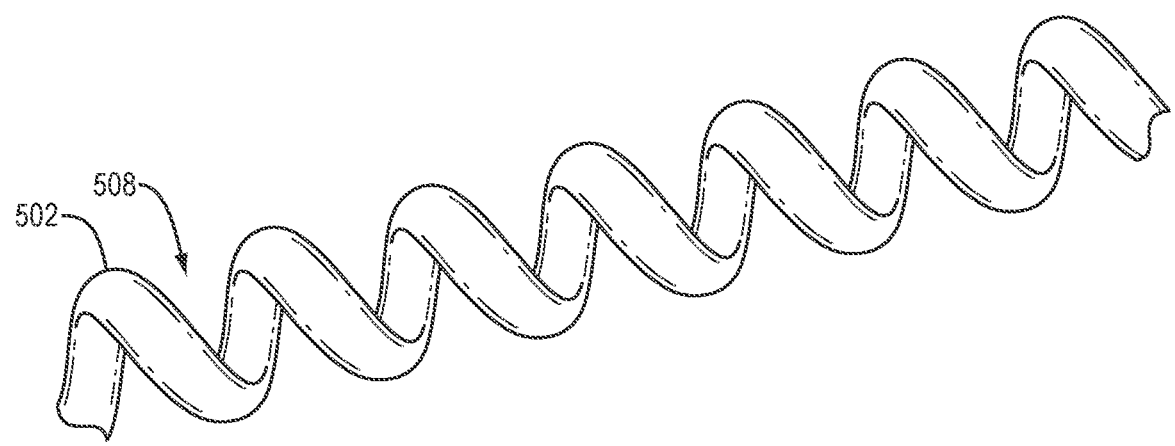
FIG. 5B illustrates a stent in accordance with an embodiment of the present disclosure including one filament under tensile stress.

Referring to FIG. 5A, an example embodiment of the present disclosure may include a stent made of one filament 502 and only one contact line 508 among coils of the single filament that may or may not be tacked. There are no groupings with one filament 502, but groupings could be simulated by tacking coils at intervals along the length. FIG. 5B illustrates a stent with a single filament in an extended state. In this configuration greater extension may be achieved, e.g., a group coils with two filaments of the same material under the same tensile stress because of a wider spacing at the contact line 508 and a lack of groups of coils. This embodiment may be desirable as a stent with more deflection and less columnar strength or rigidity for an overall less stiff stent with a greater range of extension.

Figure 6A:
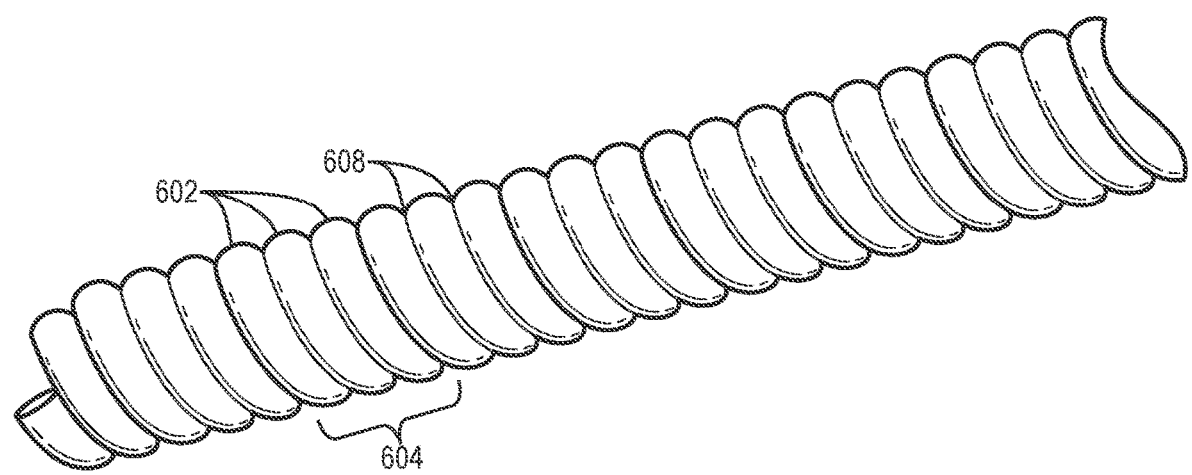
FIG. 6A illustrates a stent in accordance with an embodiment of the present disclosure including three filaments in a non-extended state.
Figure 6B:
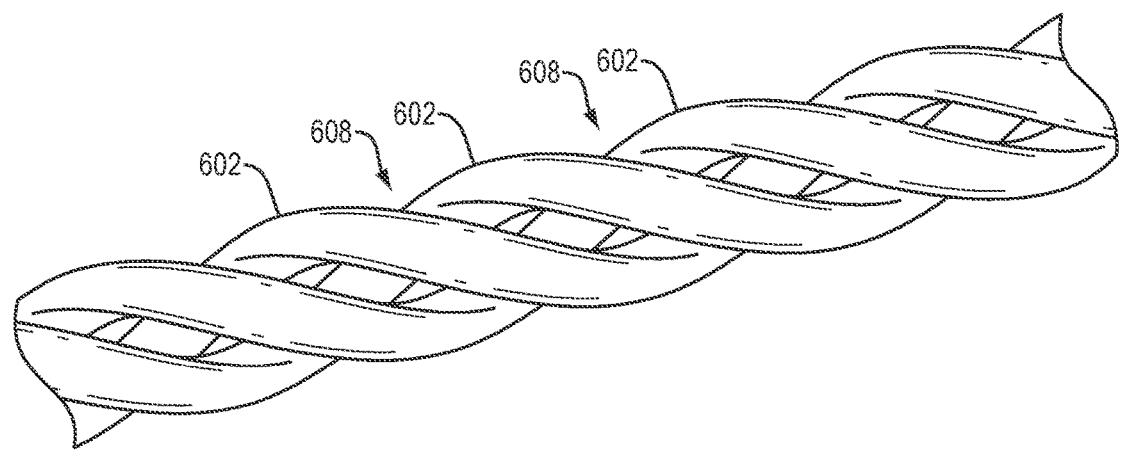
FIG. 6B illustrates a stent in accordance with an embodiment of the present disclosure including two filaments under tensile stress.

Referring to FIG. 6A, another embodiment of the disclosure may include a stent with three filaments 602 wound in adjacent groups of coils 604. These filaments 602 may or may not be tacked along any or all of the contact lines 608. FIG. 6B illustrates how such a stent substantially maintains its columnar shape under tensile stress. The filaments 602 may or may not untack from the contact lines 608. This embodiment provides relatively less deflection, higher columnar strength and rigidity for an overall stiffer stent compared, e.g., to a stent with similar filament material wound as a single filament, or wound as two filaments in adjacent groups of coils.

Figure 7:
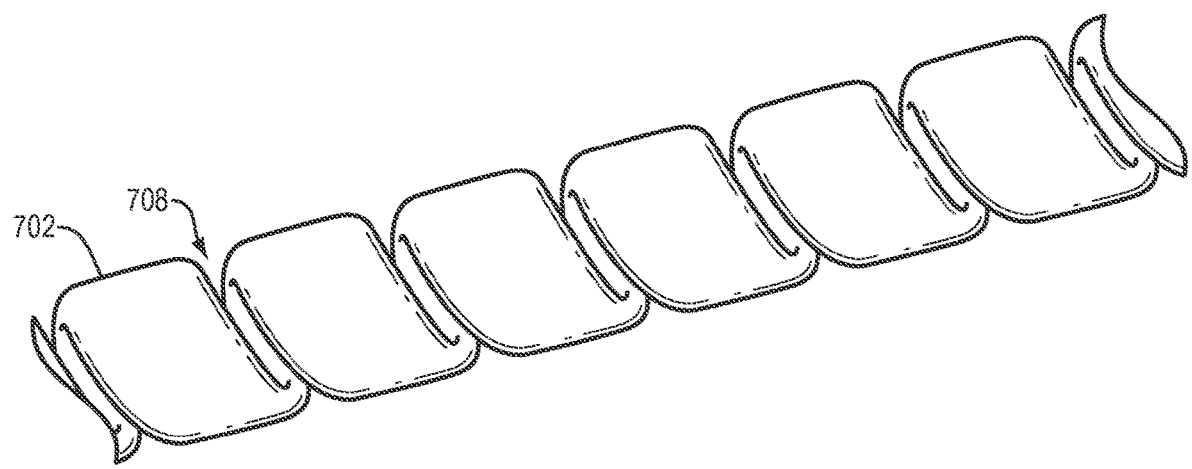
FIG. 7 illustrates a stent in accordance with an embodiment of the present disclosure including one filament in a non-extended state.

Referring to FIG. 7, another embodiment of the disclosure may include a stent made up of one or more filaments 702 with a substantially flat cross-section with rounded corners of the cross-section. Coiling this substantially flat filament creates a ribbon-like stent with contact line 708. The contact line 708 may or may not include tacking the coils of the filament to itself or to other filaments in multiple filament embodiments within or among groups (not shown). The flat or ribbon-like profile may be produced through extrusion of a flat solid or hollow profile or by extruding a solid or hollow tube and compressing the tube, e.g., as a previous embodiment described, into the flat profile In various embodiments, a stent may comprise a dissolvable coating about the filament(s) along a length of the stent. A coating may be applied to coat the interior or lumen of a stent on the inner surfaces of the filament(s), to coat the exterior of the stent or the outer surfaces of the filament(s), and/or to coat between the filament(s). Coating between the filament(s) may be either between coils of filaments within groups of coils and/or between coils in adjacent groups of coils. A coating may be applied along portions of the filament(s) or along the entire length of the filament(s). A bead coating may be drawn along at least a portion of the length of the filament(s) and/or coils. A coating may be applied along a portion of a stent or along the entire length of the stent. A coating may be applied along a body of a stent, but not along retention members of a stent. A coating may be applied to form a coating column over the filament(s) of a stent. The coating may help to tack the filament(s) and/or coils together.

A stent may be delivered over a guide wire, and so a coating within a lumen of the stent may help to reduce friction with the guide wire during proximal and distal translation of the stent along the guide wire. Coils with a coating applied may have a certain hoop strength, e.g., of more than about 1 lbf, before and for some time as the coating dissolves, and a lesser hoop strength allowing for extension, e.g., of less than about 1 lbf, after the coating dissolves. Dissolution of a coating may be designed to occur under different conditions (e.g., a certain temperature), and at a specific time or within a certain range of time. For example, it may be desirable for a coating to retain sufficient strength for about ten minutes at about 37° C. (typical body temperature). The coating may dissolve from an outer surface as water and/or other fluids penetrate and dissolve it. Dissolution may occur gradually from the outer surface inward, and may vary in time or dissolution profile depending on composition and thickness of a coating. Dissolution may occur over a matter of minutes or a matter of days. Patients may experience the highest levels of pain or discomfort within three days of implanting a stent. As such, a quickly dissolving coating may be desirable. A coating on a stent, e.g., as a column on the interior and exterior of a stent, may contribute an amount of rigidity to the stent to assist in delivering the stent as the stent is being translated, e.g., over a guide wire, and then may allow to the stent to become more flexible once the stent is in position and the coating has dissolved. However, in some cases, it may be desirable for a coating to dissolve only partially or not at all for additional rigidity or additional tacking between coils.

Suitable materials for a coating may include dissolvable materials alone, or one or more dissolvable materials in combination with non-dissolvable materials. Examples of dissolvable materials include: poly-glycolic acid, poly-lactic acid, poly-caprolactone, collagen, gelatin, polyvinyl alcohol, polyethylene glycol, branched polymers for crystallization, low molecular weight crystalline peptides, trehalose, sucrose, blends of low and high molecular weight dissolvable materials that may dissolve at different rates, water soluble hydrophilic materials, polyurethanes, polyvinylpyrrolidones, Sancure® (Sanncor Industries), Bayhydrol® (Bayer), ICE (i.e., a blend of polyurethane and polyvinylpyrrolidone), rapidly degrading polymers, biodegradable materials, enzymatically cleavable materials, and hydrolizable materials.

Figure 8:
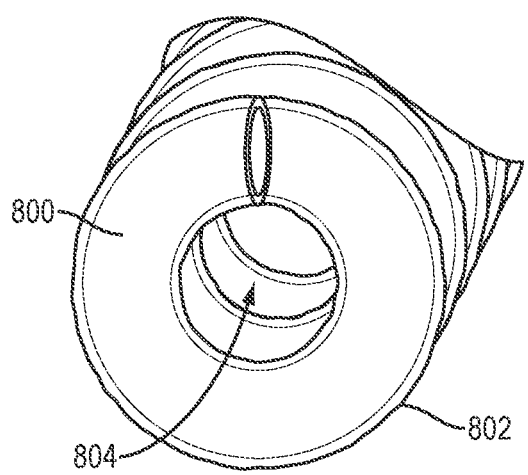
FIG. 8 illustrates a stent in accordance with an embodiment of the present disclosure including a coating.

Referring to FIG. 8, a stent with a dissolvable coating in accordance with one embodiment is depicted. The stent comprises a single filament wound in coils with a dissolvable coating 802 about the filament 800 along a length of the stent. The coating 802 is applied to the lumen 804 of the stent on the inner surfaces of the filament, the exterior of the stent or the outer surfaces of the filament 800, and between the filament coils. Certain of the coils of the filament that are adjacent to each other along the length of the stent may also be tacked together to control extension of the stent.

Figure 9:
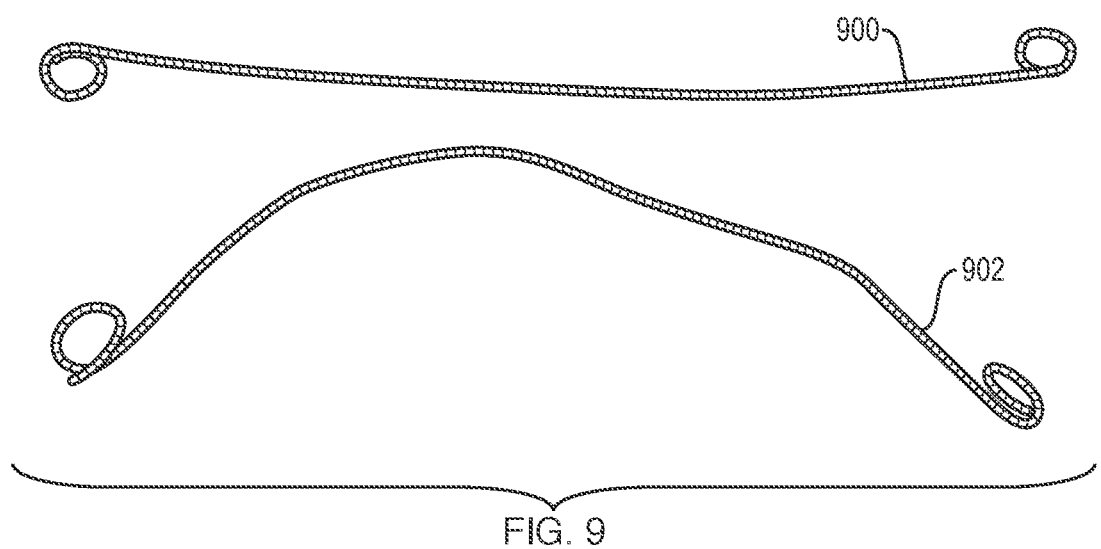
FIG. 9 illustrates a comparison of stents in accordance with embodiments of the present disclosure, the top view including a stent with a coating and the bottom view including a stent without a coating.

During stent delivery, it may be desirable that a stent be substantially straight and relatively rigid until it is in position within a patient. Once in position, it may be desirable that the stent be relatively flexible in order to comfortably function when accommodating ordinary movement of the patient's anatomy. For example, about 3 cm of ureter movement may occur during respiration or body movement. Additionally, ureter length may vary from patient to patient, and so an extension length of up to about 10 cm may be desirable. The addition of a coating to a stent may be desirable to achieve this transition from more rigid to more flexible and is intended to deliver the stent more as a column and dissolve away to leave the more flexible underlying stent. As an example, FIG. 9 illustrates a stent with a coating 900 and a stent without a coating 902. The stent with a coating 900 is straighter and more rigid than the stent without a coating 902, which is more curved and loose. The stent with a coating 900 may ease the delivery process within a patient, e.g., distal translation over a guide wire. Once the coating has dissolved and the stent with a coating 900 transitions to a stent without a coating 902, the filaments may extend and flex to accommodate the shape and extension of the ureter. A coating that covers the inside of the lumen of a stent created by the coils of filament(s), as well as the exterior of the stent, may increase the dissolution time and columnar strength of the coating.

Figure 10:
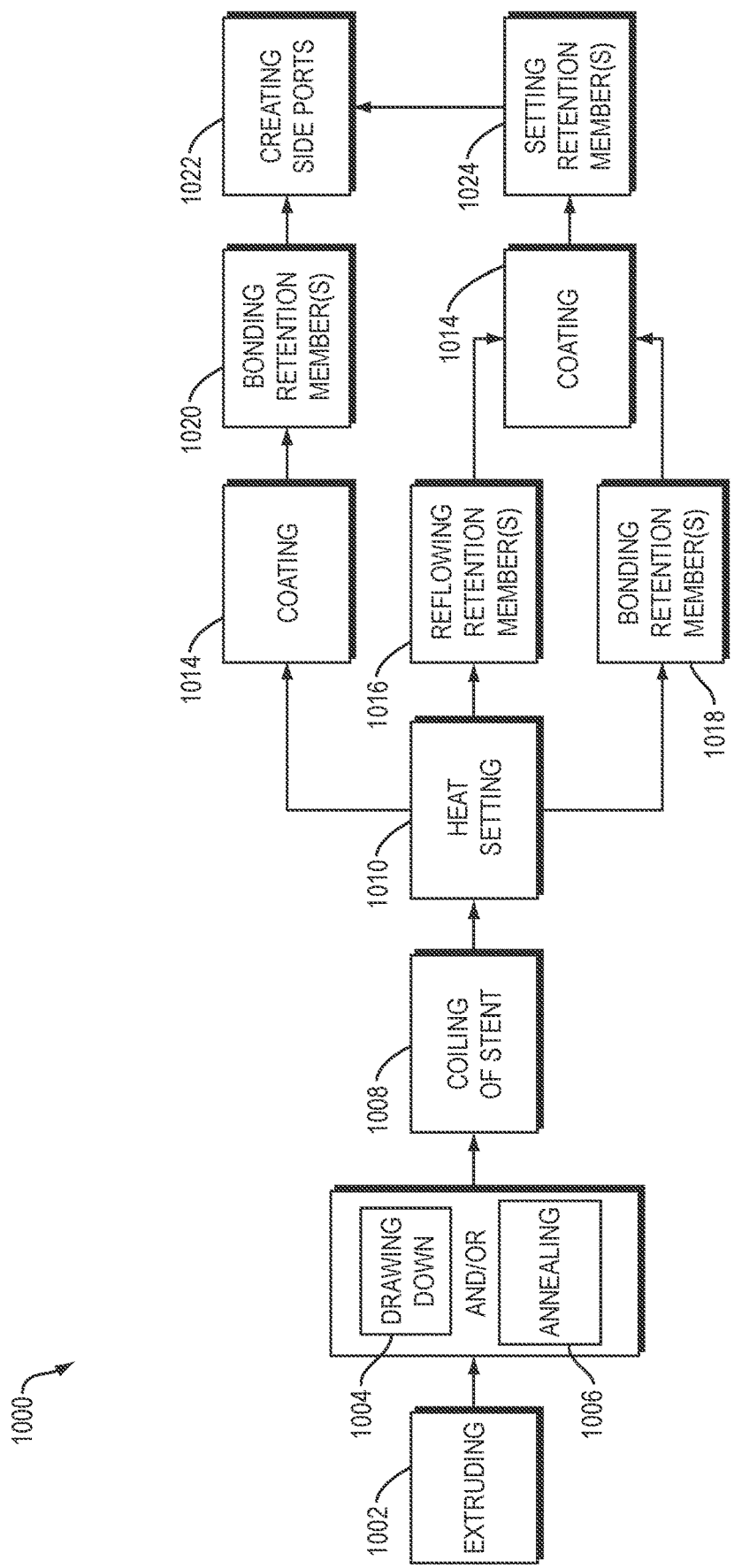
FIG. 10 illustrates methods of forming and coating a stent in accordance with embodiments of the present disclosure.

In various embodiments, methods of manufacturing a stent include applying a dissolvable coating such as polyvinyl alcohol (PVOH). Referring to FIG. 10, a method 1000 of manufacturing a stent includes extruding a filament(s) at step 1002. Extruding a filament(s) may be performed by pushing a ductile material through a die to create a substantially fixed cross-section (e.g., circular, oblong, star-shaped, etc.). The extruded filament(s) may be drawn down at step 1004 through heat and tension from a larger diameter to a smaller diameter prior to the point of fracture. This process may orient molecular structure within the filament(s) and stretch them out, reducing the amount of extension and elasticity in the final product. In addition to or in the alternative to drawing down at step 1004, the extruded filament(s) may be annealed at step 1006 through heating and slow cooling in order to remove internal stresses within the filament(s). This process may increase ductility of the filament(s) for coiling the filament(s) at step 1008. Altering the extrusion draw speed may affect the elasticity of the filament(s). The one or more filaments are coiled by, e.g., winding the filament(s) around a mandrel to form a lumen. The coiled filament(s) may be heat set at step 1010 by utilizing, e.g., a dry oven, a heated water bath, or infrared radiation. Heat setting temperatures may be material-dependent, and may be generally above the softening point of the material but below the melting point. Adjacent groups of coils of a plurality of filaments, or adjacent coils within a group, or adjacent coils of a single filament, may be tacked together at select locations along the length of the stent at or just after heat setting in step 1010. Different methods of tacking may be performed depending on the material of a stent and how the filament(s) are coiled. Coils compressed together and/or arranged with certain pitch angle(s) may tack to each other while maintained at the softening temperature point of a material or focused heat sources may be used with filament(s) at select locations to mold or reflow the material of the filament(s) of adjacent coils for tacking purposes. A softer material may more easily bond to itself than a firmer material. Coils may be permanently tacked or tacked weakly such that the filament(s) of adjacent coils may untack when subjected to pre-determined tensile and/or shear stresses.

A method 1000 of manufacturing a stent may further include setting a retention member (e.g., a pigtail) separate from the filament(s), and then bonding the retention member to the body of the coiled filaments at step 1020 after the body has been coated at step 1014. Setting the retention member(s) may be performed using, e.g., a dry oven, a heated water bath, or infrared radiation. The retention member(s) may be set at a temperature that is material dependent. A suitable temperature for typical polymer materials used with ureteral stents may be above about 75° C.

Alternatively, a set retention member may be bonded at step 1018 to one or more ends of the filament(s) by heating and melting one or more ends of the filament(s) and/or the retention member(s) together. As a further alternative, reflowing the retention member(s) at step 1016 may be performed by heating one or more ends of the filament(s) to form a retention member. Reflowing a retention member at the end of a stent may include fusing the filaments together in a substantially straight shape. A shaped retention member (e.g., a pigtail) may be formed on a mandrel. Setting retention member(s) at step 1024 may be performed by subjecting a retention member shape (e.g., a renal pigtail over a mandrel) to infrared to set or further set or tack the retention member(s) at one or both ends of the stent. Infrared may be used, when heating may be no longer desirable in the process, to avoid reflowing the material of a stent or undoing the tacking and/or coating that may have already been applied.

A method 1000 of manufacturing a stent may further include coating the stent at step 1014 with a dissolvable coating such as described above. In the alternative where the retention member is set and bonded to the stent body at step 1020, the coating step 1014 occurs prior thereto, and the coating is therefore applied only to the stent body that results from step 1010, and not the retention members. In the alternatives where the retention members are reflowed from the stent body at step 1016 or bonded to the stent body at step 1018, the coating step 1014 occurs thereafter, and the coating is therefore applied to the stent body and retention members. The stent and/or retention members may be coated once or multiple times. One or more retention members may be coated or uncoated. A coating may be formed by suspending and/or dissolving pellets of the coating material in a solution using heat and/or agitation (e.g., PVOH pellets in water). The solution may be applied to the filament(s) of the stent body and/or retention members at room temperature. Additionally, if filament coils have been tacked together, the coating should be kept at a temperature which prevents filament(s)/coil(s) from untacking. In various embodiments, a coating solution may be applied by dipping the filament(s) wound on a mandrel into solution, by spraying a solution to coat the filament(s), by cold injection mold casting a coating solution around the wound filament(s), by extruding a coating solution onto the filament(s) before coiling, etc. In order to achieve a sufficiently thick coating such that the stent may travel along a guide wire and through a body lumen without damaging the stent or losing excessive amounts of the coating, the solution may need to be viscous enough such that it adheres to the filament(s) and does not slough off. The solution may be cured to the filament(s) in an oven (e.g., at about 50° C. to 60° C. for about two to three hours). The curing temperature for the coating solution may be at a low enough range such that the stent material does not soften. Curing removes solvent (e.g., water) from the solution, creating a hard coating. Evaporating the water in the solution at a rapid rate may allow a thick coating to be maintained. Once cured, a stent from the above process may be obtained with a coating that may dissolve in about 10 minutes at about 37° C.

A method 1000, may further include creating sideports at step 1022 in the coils forming a stent. These sideports may be drilled through the coils and into the lumen created by the coils. A suture may be looped and/or tied into at least one sideport.

Although above embodiments have been described with respect to one, two, or three filaments, wound in coils, any number of filaments may be utilized as desired, depending on the dimensions, processing, and materials of the filaments and the pitch, height, and diameter of the coils, as examples, to achieve the desired flexibility and controlled extension.

A controlled extension stent may be created by winding one or more filaments in coils around a mandrel such that the filaments may alternate. This process may create a stent body with a lumen running through the length of the coiled filaments. The filaments may be tacked together at various points along the stent body using the methods described in this disclosure. The stent body may be coated with a dissolvable solution, as described above. Creating the stent may include straightening the coils at either or both end portions of the stent, fusing the filaments together along the end portions, and forming them into retention members.

Treating a patient with an embodiment of the present disclosure may be performed by introducing a controlled extension stent in accordance with the above or additional or alternative embodiments into a patient. A physician may use a cystoscope to locate the ureteral orifice where urine drains into the bladder. This may or may not be performed over an already introduced flexible guide wire, of which the stent may slide over via the lumen of the stent created by the coils of one or more filaments along the length of the stent. X-ray or fluoroscopy imaging may be used to monitor the guide wire and/or stent into the ureteral orifice and up the ureter. Contrast fluid may be injected using a soft hollow temporary stent to improve guidance. If a guide wire is used, the stent may be pushed over and along the guide wire and up into the kidney. Advancing the stent may be performed by using another instrument such as a "pusher". If a guide wire is used, it may be removed before or after the stent is in position. A retention member of a stent, if present at one or both ends of the stent, may be formed in the kidney and/or bladder. The stent may be positioned within a patient such that the stent cooperatively extends according to the length of the ureter and/or extends and contracts along with the bodily movement of the patient without migrating out of position.

In the above, alternative, or additional embodiments of the disclosure, the outer surface of a stent may be reflowed so that it is substantially smooth. This may create a thin outer skin that may or may not be easily broken upon extension. A skin of material may also be placed over the outside of the stent like a film. In this embodiment, as the inner coils of the stent extend, the outside skin will stretch so as to also extend.

In another embodiment of the present disclosure, the filaments may be spiraled inside each other in such a way that the body of the stent can telescope for additional length or compression at an end of the stent or throughout the length of the stent.

Devices may include a coating on the exterior and/or interior of the filaments, which may in certain examples be a hydrophilic or hydrophobic coating, depending on the desired handling characteristics to be imparted to the stent. Such a coating may be applied after extrusion or be integral to the manufacture of the filaments used to construct the stent. The coating may be dissolvable and applied to a stent as described above.

Materials of the filament may be polymeric in various embodiments of the present disclosure. Polymeric materials suitable for embodiments of the filament may comprise any polymer or polymer blend suitable for use in implantable or insertable medical devices. Polymers may be selected, for example, from suitable members of the following, among others: polyolefins such as polyethylenes (e.g., metallocene catalyzed polyethylenes), polypropylenes and polybutylenes; polyolefin copolymers, e.g., ethylenic copolymers such as ethylene vinyl acetate (EVA) copolymers, ethylene-methacrylic acid copolymers and ethylene-acrylic acid copolymers, where some of the acid groups can be neutralized with either zinc or sodium ions (commonly known as ionomers); vinyl aromatic polymers such as polystyrene; vinyl aromatic copolymers such as copolymers of olefins and styrene or alpha-methyl styrene, for example, butadiene-styrene copolymers and copolymers of polyisobutylene with polystyrene or polymethylstyrene, for example, polystyrenepolyisobutylene-polystyrene triblock copolymers; polyacetals; chloropolymers such as polyvinyl chloride (PVC); fluoropolymers such as polytetrafluoroethylene (PTFE); polyesters such as polyethyleneterephthalate (PET); polyester-ethers; polyamides such as nylon 6 and nylon 6,6; polyethers; polyamide ethers such as polyether block amides (PEBA) comprising (a) nylon blocks, for example, nylon 6, nylon 4/6, nylon 6/6, nylon 6/10, nylon 6/12, nylon 11 or nylon 12 blocks and (b) polyether blocks, for example, poly(ethylene oxide), poly(trimethylene oxide), poly(propylene oxide) or poly(tetramethylene oxide) blocks, one specific example of which is a poly(tetramethylene oxide)-b-polyamide-12 block copolymer, available from Elf Atochem as PEBAX; polyoctenamers such as Vestenamer® from Degussa Corp., Parsippany, N.J., which is a mixture of cyclic and linear polyoctenamers; elastomeric and thermoplastic polyurethanes, including polyurethane copolymers (including block and random copolymers that are polyether based, polyester based, polycarbonate based, aliphatic based, aromatic based and mixtures thereof), commercially available examples of which include Carbothane®, Tecoflex®, Tecothane®, Tecophilic®, Tecoplast®, Pellethane®, Chronothane® and Chronoflex®); and vinyl aromatic polymers and copolymers; silicones; polycarbonates; as well as mixtures of any of the foregoing, among others. The filaments may be made up of multiple layers of material for their properties (such as anti-encrustation, radiopacity, etc.). The filaments may be made up of differing materials from each other, may include coextensions of different materials, or may include an inner core and one or more outer layers of different materials.

EVA copolymers are one preferred group of polymers for use in ureteral stents. Examples include EVA copolymers having a vinyl acetate content of from about 5% to about 40% (including 5% to 10% to 15% to 20% to 25% to 30% to 35% to 40%, with 10-30% being typical). Increasing the vinyl acetate content typically results in a softer material, while decreasing the vinyl acetate content typically produces a harder material.

The stent of various embodiments of the present disclosure may also contain one or more optional additives, for example, selected from therapeutic agents, radiopaque agents, colorants, other optional additives such as plasticizers and extrusion lubricants, and combinations of the above, among others, in amounts effective to serve their intended purposes. Where used in the devices of the present disclosure, such optional additives may be present, for example, in the polymeric materials such as those discussed above, among others, or in coatings applied to the polymeric materials, or both.

Radiopaque agents facilitate viewing of the stent during insertion and at any point while the stent is implanted. Among radiopaque agents useful in the stents of the present disclosure are included bismuth salts such as bismuth subcarbonate, bismuth oxychloride, bismuth trioxide, barium sulfate, tungsten, and mixtures thereof. More specific examples of such radio-opaque agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine, among others. Where present, the radiopaque agent is typically present in an amount of from about 10% to about 40% (including 10% to 15% to 20% to 25% to 30% to 35% to 40%, with 15-30% being more typical). Additionally or alternatively, the polymeric material or additive material choice, as well as extrusion technique, may be optimized to enhance device contrast using ultrasound imaging. The incorporation of sonographic agents, in addition to or as an alternative to radiopaque agents, such as contrast beads or foams, among other examples, facilitate viewing of the stent under ultrasonic imaging during insertion of the device and at any point while the device is implanted. One skilled in the art can readily determine an appropriate radiopaque and sonographic agent content to achieve the desired visibility. The polymer materials described may be mixed with the radiopaque and/or the sonographic agents above, or a colorant. A colorant may be used as a visual cue to a medical professional about the location of the stent in the patient.

Examples of optional therapeutic agents include antimicrobial agents, agents that reduce pain and discomfort, such as anti-inflammatory agents, analgesic agents, local anesthetic agents and antispasmodic agents, anti-cancer agents, and combinations thereof. The term "antimicrobial agent" as used herein means a substance that kills and/or inhibits the proliferation and/or growth of microbes, particularly bacteria, fungi and yeast. Antimicrobial agents, therefore, include biocidal agents and biostatic agents as well as agents that possess both biocidal and biostatic properties. Anti-inflammatory agents include steroidal and non-steroidal anti-inflammatory agents. Analgesic agents include narcotic and non-narcotic analgesics. Examples of anticancer drugs include alkylating agents, antimetabolites, antimitotics, hormones, immunosuppressives, natural products, and other agents. Specific examples of the categories of therapeutic agents enumerated here are described in U.S. Pat. Nos. 8,728,169 and 8,597,367, assigned to Boston Scientific Corporation, the entire disclosures of which are incorporated herein by reference.

In embodiments of the present disclosure where a therapeutic agent is provided within a polymeric material, the device may exhibit an extended release profile or rapid release profile. By "extended release profile" is meant a release profile by which an effective amount of therapeutic agent continues to be released at least one day after device implantation or insertion, for example, from 1 day to 2 days to 4 days to 1 week to 2 weeks to 1 month to 2 months to 6 months to 1 year or more after device implantation. By "rapid release profile" is meant a release profile by which the therapeutic agent is substantially all released (e.g., 75% to 90% to 95% or more is released) within 24 hours of implantation or insertion, for example, from 1 hour or less to 2 hours to 4 hours to 8 hours to 16 hours to 24 hours. In certain embodiments, prior to insertion or implantation, one (e.g., a physician or an assistant to the same) may spray the device with, or dip the device into, a therapeutic-agent-containing solution, thereby loading the device with the agent. The amount of therapeutic agent present, will depend, for example, upon the efficacy of the therapeutic agent employed, the release rate, and so forth. One skilled in the art can readily determine an appropriate therapeutic agent loading to achieve a desired outcome.

In various embodiments above and otherwise in accordance with the present disclosure, the filament of a stent may include a single-piece, extruded body that is a single material having the same durometer value throughout the length of the device. Alternatively, a filament may include along the length a first section of a material having a first durometer value and a second section of a material having a second durometer value. The second durometer value may be greater than the first durometer value, such as a ureteral stent as described above, where the first section may correspond to the proximal portion and the bladder retention member and the second section may correspond to the distal portion and the renal retention member. A transition section of the filament may include a co-extrusion of the first and second materials. For example, the "hard" material can be EVA having a durometer value of about 80 to about 95 on a Shore A scale, preferably about 87 to about 95 on a Shore A scale, and more preferably about 90 on a Shore A scale, and the "soft" material can be another type of EVA having a durometer value of about 70 to about 90 on a Shore A scale, preferably about 78 to about 90 on a Shore A scale, and more preferably about 86 on a Shore A scale. Interrupted layer extrusion techniques, gradient-type coextrusion techniques, or similar techniques can be used to produce the transition sections described above.

Drainage elements may be arranged along an exterior of the stent and in fluid communication with the lumen created by the coils of the stent to facilitate drainage of fluid along the interior and exterior of the device. If the filaments are hollow, then the elements may be holes or other shapes. Also, the spacing between coils of the stent may provide for drainage. Additionally or alternatively to the drainage elements, channels may be included on the exterior to increase the drainage capabilities of the device. Channels may assume various shapes and configurations, such as semicircular, triangular, rectangular and trapezoidal cross-sections, respectively, among many other shapes. The above embodiments may also include segmented sections of coiled filaments alternating with sections of straightened filament. Additionally or in the alternative, the filaments may be formed with a braided pattern with enough structure to form a stent but also loose enough to allow for some degree of controlled extension. Even a relatively tight braided pattern may allow for some extension from the elastic and/or plastic deformation of the filament material.

Various retention members of devices according to one or more embodiments of the present disclosure may be formed by winding the one or more filaments of the elongate tubular body on a mandrel, shaping, and heat setting end portions of the coiled body in a particular form to give the end portions memory when unconstrained in the patient to assume the form of the retention member. A retention member (such as a renal retention member) may comprise a single pigtail wound in a plane that is offset from the plane that is parallel to the longitudinal axis of an intermediate portion of the stent. Other examples of retention members for use with this or other embodiments of the present disclosure include, for example, annular tails, spirals, coils, corkscrews, malecots, barbs, mushrooms and hook ends, conical shapes, among others. The retention member may be a funnel or cone-like shape at the distal end of the stent where the stent diameter gradually enlarges from the proximal end of the stent towards the distal end of the stent. The end portions forming the retention members may the filaments as they occur along the body of the stent or the filaments may be fused together and then given the form of the retention member. A filament or filaments may be formed into a desired shape by heating while on the mandrel. Alternatively, the filament or a grouping of filaments may be laid into a plate having a groove cut into it in the shape of the desired retention member. The plate may be heated from below (for example, with a heat lamp) to form the filament or stent body into a retention member shape according to the configuration of the groove. Both retention members may be formed at the same time using two adjacent plates, each with a groove for the retention member at either end of the stent. The plates may be heated at different temperatures, to the extent necessary, for example, if the two ends of the device are made from different material(s), and may be heated for the same or different lengths of time.

Although placement is described above with the retention members taking on a particular shape, in vivo, for example, upon removal of a guide wire or delivery device, or upon emergence from a channel (e.g., due to elastic rebound of the material), the shape may also be attained by application of an external stimulus such as heat or light (e.g., where a shape memory material such as a heat or light activated shape memory polymer is employed). The heat or light may be applied prior to or after the desired length of the stent is adjusted.

In various embodiments of the present disclosure, and as described above, positioning of the stent at a desired point of placement may be accomplished by different configurations of delivery devices known in the art. For example, with respect to a ureteral stent as an exemplary embodiment of the present disclosure, the distal end of the stent may be inserted through the bladder and ureter into the kidney. A medical professional may insert a guide wire through the bladder, ureter and up into the kidney. The stent is placed over the guide wire, thereby straightening the retention members on the wire. The stent slides along the guide wire alone or is carried on a catheter or other delivery device that the wire extends through. The guide wire, if used alone, may be sufficiently stiff to hold the retention members straight while the guide wire is in the lumen of the stent. An outer pusher member slidably coaxial with an inner member of a delivery device, or with a wire if used alone, may be used to abut the proximal end of the stent and push the stent distally.

A radiopaque or sonographic band, filler or other marker as part of the pusher and/or delivery device allows a medical professional to view the pusher and/or device on a fluoroscope or using ultrasound. Additionally, if the stent is radiopaque or sonovisible, placement of the stent in the patient may be confirmed by viewing the stent on a fluoroscope or using ultrasound. Once positioned at distal end of the placement point, the guide wire alone or in conjunction with a delivery device, if used, is withdrawn from the lumen of the distal (or kidney, in the case of a ureteral stent) retention member. If a pusher is used, the pusher holds the stent in place while the guide wire or guide wire and inner member of the delivery device is removed. The shape-memory material from which the retention member is constructed allows the retention member to return to its shape memory configuration, such as a pigtail coil.

As the guide wire and/or delivery device is withdrawn into, for example, the bladder in the case of a ureteral stent, the medical professional sights the renal retention member and proximal portion including the graduated markings corresponding to incremental portions along the length thereof, identifying the graduated marking that approximates the desired length of the stent extending along the ureter at the placement point.

A spiral cone-shaped tip on the distal retention member can facilitate inserting the device through the passages of a patient's body. Additionally, a professional may use a suture to reposition the stent (by pulling on it) when inserting the stent, and the professional may use a suture to remove the stent from the patient after some period of use. For example, a professional may leave the proximal end of the suture inside the patient's body or leave the end of the suture outside the body. When the stent is to be removed, the professional may pull on the suture to remove the stent. However, other means may be used to remove the stent.

Additional or alternative materials, coatings, fillers, agents, retention members and like suitable for the devices of the present disclosure are known in the art and may be applied hereto, including as described in U.S. Pat. Nos. 8,728,169; 8,597,367; 7,951,206; and 5,681,274, assigned to Boston Scientific Corporation, the entire disclosures of which are incorporated herein by reference.

Devices according to the embodiments described, and in accordance with other embodiments of the present disclosure, alone or in a system or kit or as part of a method or procedure, including with other accessories, may be used in cavities, lumens, tracts, vessels and organs of the body, aside from stenting the ureter, such as procedures to drain, access or otherwise treat or diagnose conditions in the peritoneal, abdominal, bronchial or thoracic cavities, vascular vessels, gastrointestinal or urinary tract, uterus, bladder, lung and liver organs, etc.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. A flexible controlled extension stent configured to allow controlled extension in response to bodily movement when implanted in a body lumen, the stent comprising:
   a filament wound into a plurality of coils defining a lumen about a longitudinal axis of the stent along the length of the stent;
   wherein:
   two or more adjacent coils are in separable contact, and two or more coils are attached together in separable contact;
   the stent is expandable along the length thereof, in response to bodily movement, from a longitudinally non-extended state in which the two or more adjacent coils are in substantial contact with one another and the two or more attached coils are attached together, to a first longitudinally extended state in which the two or more adjacent coils separate to no longer be in contact but the two or more attached coils are still attached together, and from the first longitudinally extended state to a second longitudinally extended state in which the two or more adjacent coils are separated from one another and the two or more coils which were attached together in the non-extended state and the first extended state separate to no longer be attached together to accommodate movement of the body lumen in which the flexible controlled extension stent is implanted.

2. The stent of claim 1, wherein the attached coils are tacked together on at least one substantially helical contact line running between the coils along at least portions of the stent length.

3. The stent of claim 2, further comprising a reflowed substantially smooth outer surface along the at least one substantially helical contact line.

4. The stent of claim 1, wherein the two or more attached coils of the filament are tacked together.

5. The stent of claim 1, wherein a proximal and a distal end of the stent each have an annular tail.

6. The stent of claim 1, wherein coils at a distal end of the stent form a spiraled cone-shape, the cone-shape widening in diameter toward the distal end of the stent.

7. The stent of claim 1, wherein the attached coils are tacked together and the adjacent coils are not tacked together.

8. The stent of claim 1, further comprising a dissolvable coating along the length of the stent in at least the non-extended state, wherein the coating is disposed about portions of the filament.

9. The stent of claim 8, wherein the coating comprises polyvinyl alcohol.

10. The stent of claim 1, wherein the difference in length between the longitudinally extended state and the non-extended state is a range of about three centimeters to about ten centimeters.

11. The stent of claim 1, wherein certain of the coils overlap each other in a telescoping fashion.

12. The stent of claim 1, wherein certain of the coils lie in a plane substantially perpendicular to the longitudinal axis.

13. The stent of claim 1, wherein certain of the coils lie in a plane at an angle from the longitudinal axis that ranges from 10 degrees to 90 degrees.

14. A flexible controlled extension stent configured to allow controlled extension in response to bodily movement when implanted in a body lumen the stent comprising:
   a filament wound into a plurality of coils about a longitudinal axis of the stent and along the length of the stent in a substantially helical pattern, the coils defining a lumen along the longitudinal axis through the center of the pattern, wherein:
   the stent is expandable along the length thereof, in response to bodily movement, between a first state in which a first group of two or more adjacent coils of the filament are in contact with one another but not attached to one another, and a second group of two or more of the coils are connected together along a contact line as the connected coils wind along the length of the stent, and a second longitudinally extended state in which adjacent coils in the first group separate to be spaced apart from one another and no longer in contact and coils in the second group remain connected together along the contact line and are separable from one another upon application of further longitudinal force to pull the coils in the second group apart.

15. The stent of claim 14, wherein the filament has a substantially flattened rectangular cross-section with rounded corners.

16. The stent of claim 14, wherein the filament is a ribbon wound in the adjacent coils.

17. The stent of claim 14, wherein the two or more connected coils of the filament are tacked together at intervals along the length of the stent.

* * * * *